(12) United States Patent
Tachibana et al.

(10) Patent No.: US 8,901,520 B2
(45) Date of Patent: Dec. 2, 2014

(54) PARTICLE BEAM IRRADIATION APPARATUS

(71) Applicant: Sumitomo Heavy Industries, Ltd., Tokyo (JP)

(72) Inventors: Masanori Tachibana, Niihama (JP); Junichi Inoue, Niihama (JP); Shoubun Hara, Yokosuka (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 14/331,564

(22) Filed: Jul. 15, 2014

(65) Prior Publication Data
US 2014/0319368 A1  Oct. 30, 2014

Related U.S. Application Data

(63) Continuation of application No. PCT/JP2013/051474, filed on Jan. 24, 2013.

(30) Foreign Application Priority Data

Feb. 6, 2012  (JP) .................................. 2012-023127

(51) Int. Cl.
*A61N 5/10* (2006.01)
*H01J 37/304* (2006.01)

(52) U.S. Cl.
CPC .............. *A61N 5/1075* (2013.01); *H01J 37/304* (2013.01)

USPC ....................................................... 250/492.3

(58) Field of Classification Search
USPC ....................................................... 250/492.3
See application file for complete search history.

(56) References Cited

U.S. PATENT DOCUMENTS 4,936,968 A * 6/1990 Ohnishi et al. ........... 204/192.34

FOREIGN PATENT DOCUMENTS

JP       03-117116 A     5/1991
JP       2006-288875 A   10/2006

OTHER PUBLICATIONS

International Search Report dated Feb. 19, 2013 corresponding to International Patent Application No. PCT/JP2013/051474.
English translation of PCT International Preliminary Report on Patentability dated Aug. 12, 2014 corresponding to International Patent Application No. PCT/JP2013/051474.

* cited by examiner

*Primary Examiner* — Kiet T Nguyen
(74) *Attorney, Agent, or Firm* — Squire Patton Boggs (US) LLP

(57) ABSTRACT

A particle beam irradiation apparatus including: a scanning unit configured to scan a particle beam; an electric current supply unit configured to supply an electric current to the scanning unit; and a scanning control unit configured to control the scanning unit by sending an electric current command value to the electric current supply unit, wherein a period of an operation clock of the scanning control unit and a period of an operation clock of the electric current supply unit are the same.

3 Claims, 5 Drawing Sheets

Fig.2
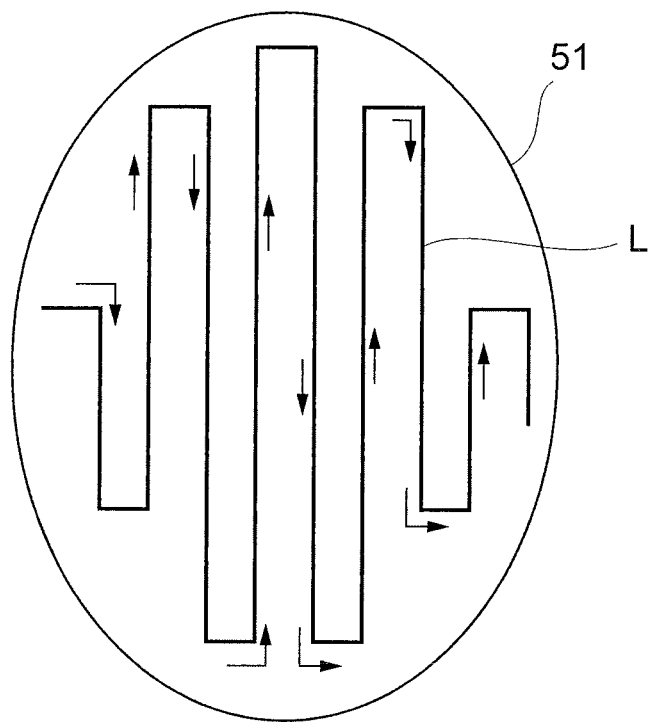
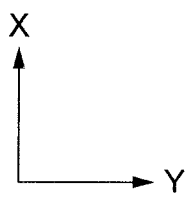

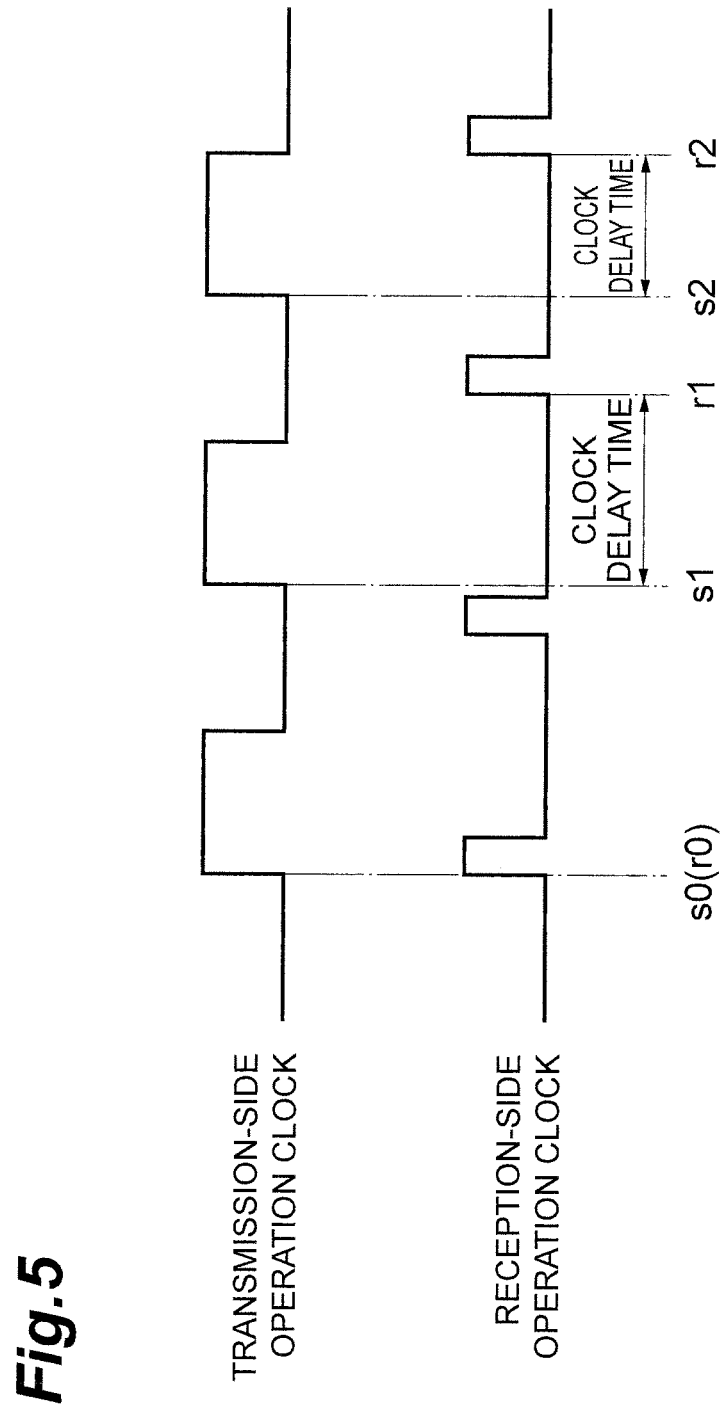

PARTICLE BEAM IRRADIATION APPARATUS

INCORPORATION BY REFERENCE

Priority is claimed to Japanese Patent Application No. 2012-023127, filed Feb. 6, 2012, and International Patent Application No. PCT/JP2013/051474, the entire content of each of which is incorporated herein by reference.

BACKGROUND

1. Technical Field

The present invention relates to a particle beam irradiation apparatus for irradiating an irradiated body with a particle beam.

2. Description of the Related Art

As a particle beam irradiation apparatus which is used for radiation therapy for a tumor or the like, a particle beam irradiation apparatus described in, for example, the related art is known. The particle beam irradiation apparatus is provided with scanning means (an electromagnet) for performing particle beam scanning, electric current supply means (a power supply) for supplying an electric current to the scanning means, and scanning control means (a command value transmission section) for controlling the particle beam scanning by the scanning means by sending an electric current command value to the electric current supply means. In the particle beam irradiation apparatus, the scanning control means sends the electric current command value to the electric current supply means on the basis of a treatment plan planned beforehand, whereby the electric current supply to the scanning means by the electric current supply means is changed, and thus scanning control of the particle beam along the treatment plan is performed.

SUMMARY

Therefore, according to an embodiment of the present invention, there is provided a particle beam irradiation apparatus including: a scanning unit configured to scan a particle beam; an electric current supply unit configured to supply an electric current to the scanning unit; and a scanning control unit configured to control the scanning unit by sending an electric current command value to the electric current supply unit, wherein a period of an operation clock of the scanning control unit and a period of an operation clock of the electric current supply unit are the same.

BRIEF DESCRIPTION OF THE DRAWINGS

FIG. 2 is a diagram for describing scanning irradiation by a particle beam.

FIG. 5 is a diagram for describing variation in clock delay time.

DETAILED DESCRIPTION

Figure 1:
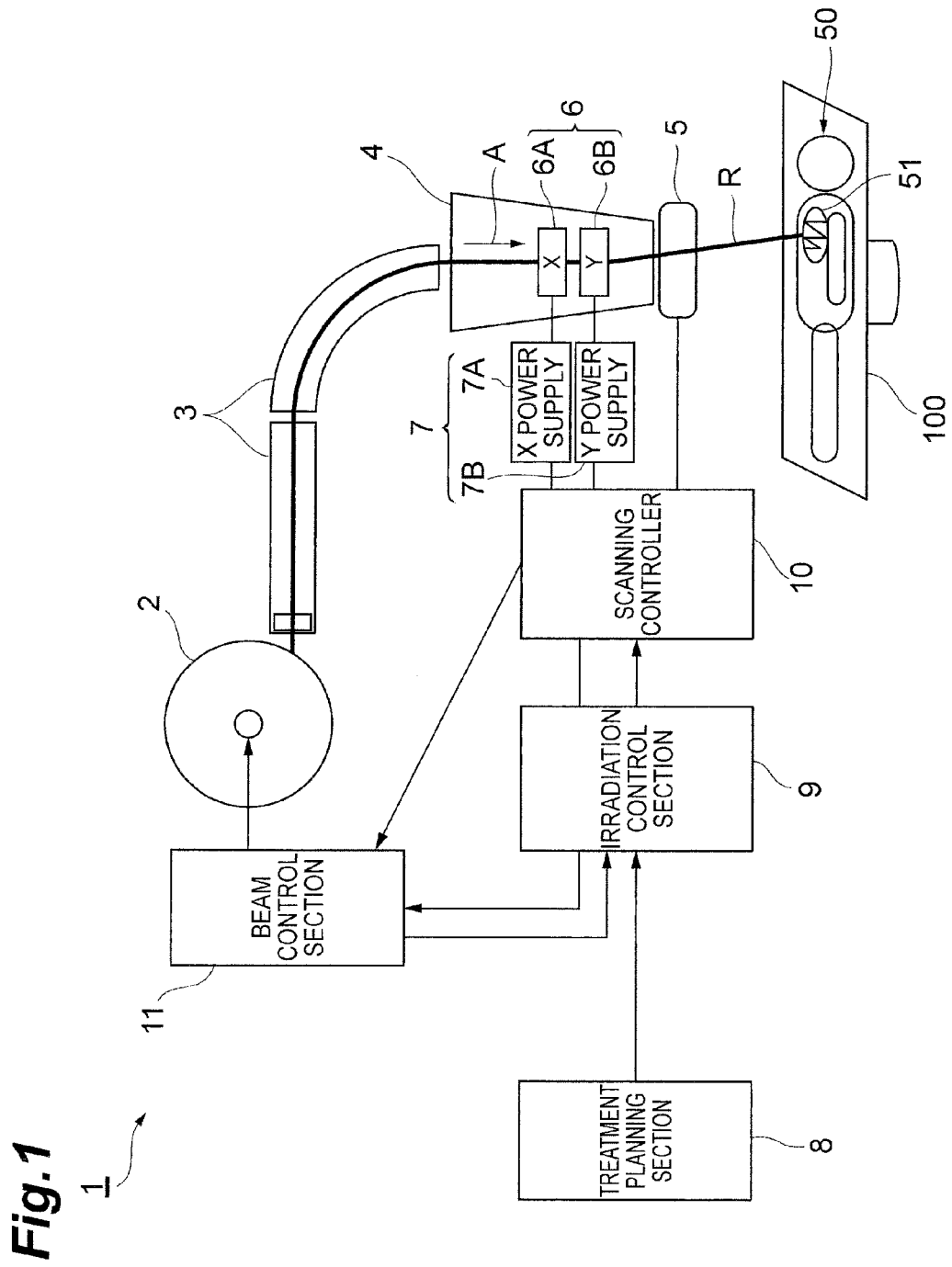
FIG. 1 is a diagram showing an embodiment of a particle beam irradiation apparatus according to the present invention.

Incidentally, in radiation beam therapy, if misalignment occurs between particle beam scanning in a prior treatment plan and actual particle beam scanning, an excessive or deficient irradiation dose occurs according to the site of a tumor, and thus a problem such as an insufficient treatment effect being obtained occurs. For this reason, in a particle beam irradiation apparatus, improvement in the accuracy of the scanning control of a particle beam is strongly desired.

Therefore, it is desirable to provide a particle beam irradiation apparatus in which it is possible to perform high-precision scanning control of a particle beam.

The inventors of the present invention have found, as a result of repeating an extensive investigation, that there is variation in the delay time after a scanning control unit sends an electric current command value to an electric current supply unit and before a scanning unit supplied with an electric current from the electric current supply unit actually performs particle beam scanning. Such variation in delay time contributes to a decrease in the accuracy of the scanning control.

As a result of repeating a further investigation, the inventors of the present invention have found that variation in delay time is caused by a difference between an operation clock of the scanning control unit and an operation clock of the electric current supply unit. Specifically, the inventors have found that variation which is caused by a difference between the operation clock of the scanning control unit and the operation clock of the electric current supply unit, of the delay time after the scanning control unit transmits an electric current command value and before the scanning unit actually performs the particle beam scanning, is a cause of variation in the entire delay time.

FIG. 5 is a diagram for describing variation in clock delay time. In FIG. 5, transmission timings of an electric current command value in a transmission-side operation clock are shown as s0 to s2. Further, reception timings of the electric current command value in a reception-side operation clock are shown as r0 to r2. As shown in FIG. 5, in a case where the period of the transmission-side operation clock and the period of the reception-side operation clock are different from each other, delay time between the transmission timing of the electric current command value by the scanning control unit and the reception timing of the electric current command value by the electric current supply unit occurs with variation.

According to the particle beam irradiation apparatus related to the embodiment of the present invention, the period of the operation clock of the scanning control unit and the period of the operation clock of the electric current supply unit are the same, and thus it is possible to make delay time between the operation clocks of the scanning control unit and the electric current supply unit constant, and thus it is possible to avoid occurrence of variation in the delay time after the scanning control unit transmits the electric current command value and before the scanning unit actually performs the particle beam scanning. For this reason, according to the particle beam irradiation apparatus described above, it is possible to avoid a situation where due to variation in delay time, the particle beam is irradiated for a longer time than a treatment plan at a certain irradiation position and the particle beam is irradiated for a shorter time than the treatment plan at the other irradiation position. Therefore, according to the particle beam irradiation apparatus described above, it is possible to perform the high-precision scanning control of the particle beam which accurately controls the irradiation time at each irradiation position on the basis of the treatment plan.

In the particle beam irradiation apparatus described above, according to an embodiment of the present invention, a configuration is also acceptable in which the scanning control unit has a transmission section configured to transmit an operation clock signal to the electric current supply unit and the electric current supply unit has a receiving section configured to receive the operation clock signal transmitted from the transmission section.

According to the particle beam irradiation apparatus described above, by transmitting the operation clock signal from the transmission section of the scanning control unit to the receiving section of the electric current supply unit, it is possible to drive the electric current supply unit by the operation clock having the same period as the operation clock of the scanning control unit. Therefore, in the particle beam irradiation apparatus described above, it is not necessary to separately provide an operation clock signal transmission section for matching the periods of the operation clock of the scanning control unit and the operation clock of the electric current supply unit, and thus it is possible to attain simplification of an apparatus configuration.

In the particle beam irradiation apparatus described above, the particle beam irradiation apparatus may further include position measuring unit configured to measure a position of the particle beam scanned by the scanning unit, and the scanning control unit may determine whether or not there is an abnormality in a scanning by the scanning unit, on the basis of a comparison result between a plan position of the particle beam corresponding to the electric current command value and a measurement position of the particle beam measured by the position measuring unit.

According to the particle beam irradiation apparatus described above, it is possible to make the delay time almost constant by suppressing variation in the delay time, and thus it becomes possible to obtain, by calculation, the influence of the delay time on the position of the particle beam, and it is possible to exactly compare the plan position of the particle beam with the actual measurement position. Therefore, according to the particle beam irradiation apparatus described above, it is possible to properly determine whether or not there is an abnormality in the scanning control of the particle beam, on the basis of a comparison result between a plan position of the particle beam and a measurement position of the particle beam.

According to the embodiment of the present invention, it is possible to perform high-precision scanning control of the particle beam.

Hereinafter, a preferred embodiment of a particle beam irradiation apparatus according to the present invention will be described in detail with reference to the drawings.

As shown in FIGS. 1 and 2, a charged particle beam therapy apparatus (a particle beam irradiation apparatus) 1 according to the above embodiment is for performing radiation therapy by irradiating a charged particle beam R with respect to a tumor (an irradiated body) 51 of a patient 50 on a treatment table 100. As the charged particle beam R, a proton beam, a heavy particle (heavy ion) beam, or the like can be given.

The charged particle beam therapy apparatus 1 performs continuous irradiation or intermittent irradiation of the charged particle beam R by a scanning method. Specifically, the charged particle beam therapy apparatus 1 performs continuous irradiation (raster scanning or line scanning) or intermittent irradiation (spot scanning) while virtually dividing the tumor 51 into a plurality of layers in a depth direction and performing scanning of the charged particle beam R along a scanning pattern L set to each layer.

The charged particle beam therapy apparatus 1 is provided with an accelerator 2 which accelerates charged particles and emits the charged particle beam R, a transport line 3 which transports the charged particle beam R emitted from the accelerator 2, an irradiation section 4 which irradiates the charged particle beam R transported by the transport line 3, toward the tumor of the patient, and a position measurement monitor (a position measuring unit) 5 for measuring an irradiation position of the charged particle beam R which is irradiated from the irradiation section 4.

The accelerator 2 emits the charged particle beam R by accelerating particles with an electric charge. As the accelerator 2, for example, a cyclotron, a synchrotron, a synchrocyclotron, or a linear accelerator can be used.

The charged particle beam R emitted from the accelerator 2 is transported to the irradiation section 4 by the transport line 3. A traveling direction of the charged particle beam R transported from the transport line 3 into the irradiation section 4 is indicated by an arrow A.

The irradiation section 4 performs the irradiation of the charged particle beam R toward the tumor 51 in the body of the patient 50 on the treatment table 100. The irradiation section 4 is provided with a scanning electromagnet (a scanning unit) 6 for performing the scanning of the charged particle beam R. In the scanning electromagnet 6, the scanning of the charged particle beam R is performed by a change in magnetic field. The scanning electromagnet 6 has a first scanning electromagnet 6A which performs the scanning of the charged particle beam R in an X direction perpendicular to the traveling direction A, and a second scanning electromagnet 6B which performs the scanning of the charged particle beam R in the traveling direction A and a Y direction perpendicular to the X direction.

The scanning electromagnet 6 is supplied with an electric current from a scanner power supply (an electric current supply unit) 7 disposed outside the irradiation section 4. The scanner power supply 7 changes an electric current which is supplied to the scanning electromagnet 6, according to an electric current command value from a scanning controller 10 (described later). The scanner power supply 7 has a first power supply (an X power supply) 7A which supplies an electric current to the first scanning electromagnet 6A, and a second power supply (a Y power supply) 7B which supplies an electric current to the second scanning electromagnet 6B.

The position measurement monitor 5 measures the irradiation position of the charged particle beam R (a position in an X-Y plane perpendicular to the travel direction A of the charged particle beam R) scanned by the scanning electromagnet 6. The position measurement monitor 5 is provided with a lattice-shaped wire grid made of a large number of wires extending in the X direction or the Y direction and measures the irradiation position of the charged particle beam R by detecting electric charges generated by the contact of the charged particle beam R with the wire grid.

Next, irradiation control of the charged particle beam R in the charged particle beam therapy apparatus 1 will be described. The charged particle beam therapy apparatus 1 has a treatment planning section 8, an irradiation control section 9, the scanning controller (a scanning control unit) 10, and a beam control section 11.

In the treatment planning section 8, a treatment plan for treating the tumor 51 of the patient 50 is created. The treatment planning section 8 creates the treatment plan on the basis of various types of data input thereto. In the treatment plan, the scanning pattern L of the charged particle beam R of each layer obtained by virtually dividing the tumor 51 into a plurality of layers in the depth direction is included. In the scanning pattern L, scanning position information of the charged particle beam R for each predetermined time is included.

The irradiation control section 9 controls the irradiation of the charged particle beam R on the basis of the treatment plan created by the treatment planning section 8. The irradiation control section 9 transmits information about the treatment plan obtained from the treatment planning section 8 to the scanning controller 10.

Further, the irradiation control section 9 transmits an emission preparation signal to the beam control section 11 on the basis of a demand signal from the scanning controller 10. The beam control section 11 starts emission preparation of the charged particle beam R by controlling the accelerator 2 in a case of receiving the emission preparation signal. The beam control section 11 transmits an emission preparation completion signal to the irradiation control section 9 and the scanning controller 10 in a case where the emission preparation of the charged particle beam R is completed.

Figure 3:
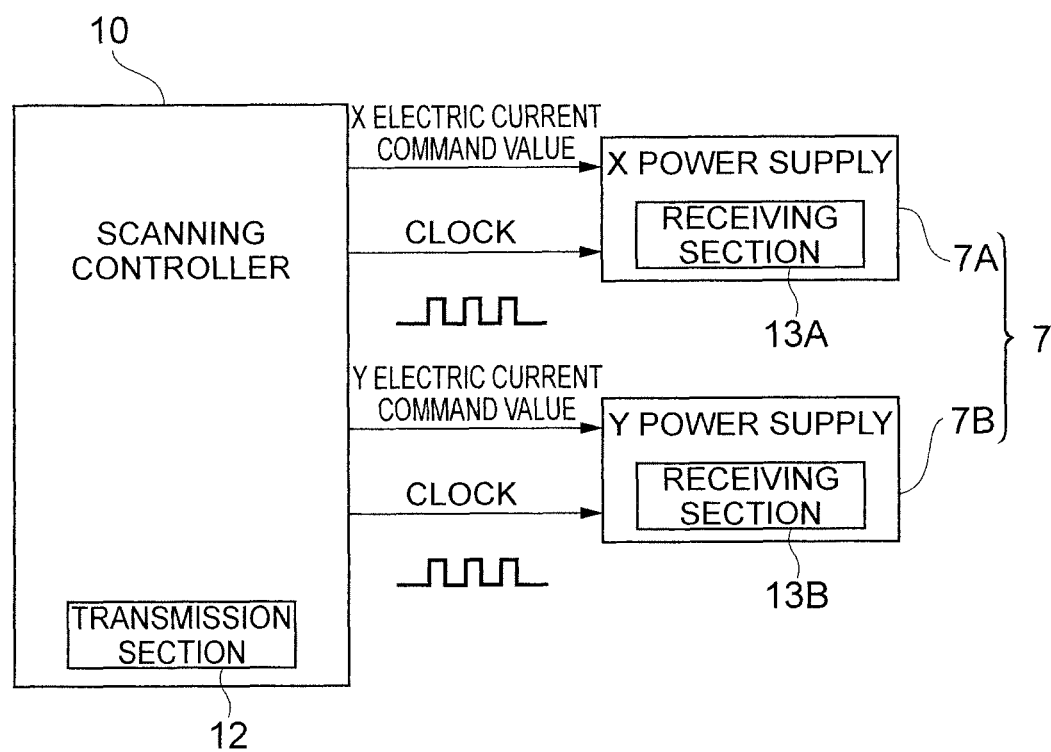
FIG. 3 is a diagram for describing a signal that a scanning controller transmits to a scanner power supply.

As shown in FIGS. 1 and 3, the scanning controller 10 performs the scanning control of the charged particle beam R on the basis of treatment plan information transmitted from the irradiation control section 9. The scanning controller 10 transmits the electric current command value according to the treatment plan to the scanner power supply 7. The scanning controller 10 indirectly controls the scanning of the charged particle beam R by the scanning electromagnet 6 by changing the electric current supply from the scanner power supply 7 to the scanning electromagnet 6 by the electric current command value.

The scanning controller 10 transmits a first electric current command value (an X electric current command value) for performing the scanning of the charged particle beam R in the X direction to the first power supply 7A. Similarly, the scanning controller 10 transmits a second electric current command value (a Y electric current command value) for performing the scanning of the charged particle beam R in the Y direction to the second power supply 7B.

Further, the scanning controller 10 is driven with an internal basis clock thereof as an operation clock. The scanning controller 10 has a transmission section 12 which transmits its own operation clock signal to the scanner power supply 7. The transmission section 12 transmits the operation clock signal to the scanner power supply 7 in order to make the period of an operation clock of the scanner power supply 7 equal to the period of an operation clock of the scanning controller 10.

On the other hand, the X power supply 7A and the Y power supply 75 of the scanner power supply 7 respectively have receiving sections 13A and 133 which receive the operation clock signal. In the X power supply 7A and the Y power supply 7B, the receiving sections 13A and 13B receive the operation clock signal transmitted from the transmission section 12 and the supply of an electric current to the scanning electromagnet 6 is performed by an operation clock having the same period as the operation clock of the scanning controller 10. Specifically, operation clocks of the operation clock signals received by the receiving sections 13A and 13B are used as the operation clocks of the X power supply 7A and the Y power supply 7B. Alternately, the operation clocks of the X power supply 7A and the Y power supply 7B are synchronized with the operation clocks of the operation clock signals received by the receiving sections 13A and 13B. In addition, the expression, the same period, is not limited to the periods being strictly the same, and an error less than or equal to 10 μs is allowed.

Further, the scanning controller 10 obtains information about a measurement position of the charged particle beam R from the position measurement monitor 5. The scanning controller 10 performs the comparison of a plan position of the charged particle beam R according to the treatment plan (a plan position of the charged particle beam R corresponding to the electric current command value) with the measurement position of the charged particle beam R obtained from the position measurement monitor 5.

The scanning controller 10 determines whether or not there is an abnormality in the scanning control of the charged particle beam R, on the basis of a comparison result between the plan position and the measurement position of the charged particle beam R. Specifically, the scanning controller 10 determines whether or not there is an abnormality in the scanning control, by determining whether or not a difference between the measurement position of the charged particle beam R and the plan position of the charged particle beam R is within an allowable range.

The scanning controller 10 stops the irradiation of the charged particle beam R by transmitting an irradiation stop signal to the beam control section 11 in a case where it is determined that there is an abnormality in the scanning control.

According to the charged particle beam therapy apparatus 1 related to the embodiment described above, since the period of the operation clock of the scanning controller 10 and the period of the operation clock of the scanner power supply 7 are the same, variation in delay time due to a difference in the operation clock is not generated, and it is possible to obtain a constant delay time after the scanning controller 10 transmits the electric current command value and before the scanning unit actually performs particle beam scanning.

Figure 4:
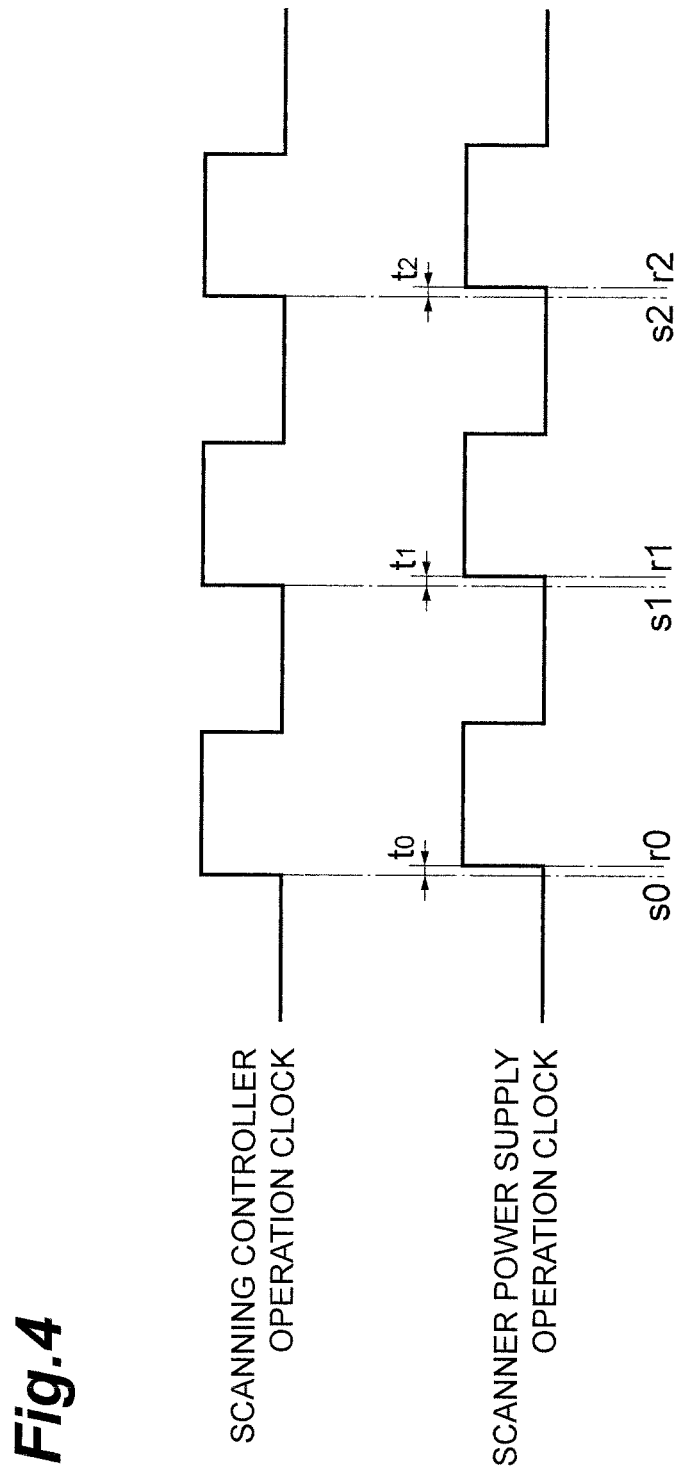
FIG. 4 is a diagram showing an operation clock of the scanning controller and an operation clock of the scanner power supply.

Here, FIG. 4 is a diagram showing the operation clock of the scanning controller 10 and the operation clock of the scanner power supply 7. In FIG. 4, transmission timings of the electric current command value in the operation clock of the scanning controller 10 are shown as s0 to s2. Further, reception timings of the electric current command value in the operation clock of the scanner power supply 7 are shown as r0 to r2. In addition, the delay time between the transmission timing s0 and the reception timing r0 is shown as t0, the delay time between the transmission timing s1 and the reception timing r1 is shown as t1, and the delay time between the transmission timing s2 and the reception timing r2 is shown as t2.

As shown in FIG. 4, in the charged particle beam therapy apparatus 1 according to the embodiment, since the period of the operation clock of the scanning controller 10 and the period of the operation clock of the scanner power supply 7 are the same, it is possible to make the delay times t0 to t2 between the operation clocks of the scanning controller 10 and the scanner power supply 7 constant, and thus it is possible to avoid the generation of variation in the delay time after the scanning controller 10 transmits the electric current command value and before the scanning electromagnet 6 actually performs the particle beam scanning. For this reason, according to the charged particle beam therapy apparatus 1, it is possible to avoid a situation where due to variation in delay time, the particle beam is irradiated for a longer time than the treatment plan at a certain irradiation position and the particle beam is irradiated for a shorter time than the treatment plan at the other irradiation position. Therefore, according to the charged particle beam therapy apparatus 1, it is possible to perform the high-precision scanning control of the particle beam which accurately controls the irradiation time at each irradiation position on the basis of the treatment plan.

Further, in the charged particle beam therapy apparatus 1, by transmitting the operation clock signal from the scanning controller 10 to the scanner power supply 7, it is possible to drive the scanner power supply 7 by the operation clock having the same period as the operation clock of the scanning controller 10. Therefore, according to the charged particle beam therapy apparatus 1, it is not necessary to separately provide an operation clock signal transmission section for matching the periods of the operation clock of the scanning controller 10 and the operation clock of the scanner power supply 7, and therefore, it is possible to attain simplification of an apparatus configuration.

In addition, in the charged particle beam therapy apparatus 1, since it is possible to make the delay time almost constant by suppressing variation in the delay time after the scanning controller 10 transmits the electric current command value and before the scanning electromagnet 6 actually performs the scanning of the charged particle beam R, it becomes possible to obtain, by calculation, the influence of the delay time on the irradiation position of the charged particle beam R. Therefore, according to the charged particle beam therapy apparatus 1, since it is possible to exactly compare the plan position of the charged particle beam R with the actual measurement position, it is possible to determine whether or not the charged particle beam R deviates from the plan position beyond the allowable range, and it is possible to properly determine whether or not there is an abnormality in the scanning control of the charged particle beam R.

The present invention is not limited to the embodiment described above. In the embodiment described above, the charged particle beam therapy apparatus 1 which irradiates a proton beam, a heavy particle (heavy ion) beam, or the like has been described. However, the present invention can also be applied to a particle beam irradiation apparatus which irradiates other particle beams.

Further, a configuration is also acceptable in which the transmission section which transmits the operation clock is provided separately from the scanning controller and the scanner power supply and both the scanning controller and the scanner power supply have the receiving sections.

The embodiment of the present invention is applicable to a particle beam irradiation apparatus in which it is possible to perform the high-precision scanning control of a particle beam.

It should be understood that the invention is not limited to the above-described embodiment, but may be modified into various forms on the basis of the spirit of the invention. Additionally, the modifications are included in the scope of the invention.

What is claimed is:

1. A particle beam irradiation apparatus comprising:
a scanning unit configured to scan a particle beam;
an electric current supply unit configured to supply an electric current to the scanning unit; and
a scanning control unit configured to control the scanning unit by sending an electric current command value to the electric current supply unit,
wherein a period of an operation clock of the scanning control unit and a period of an operation clock of the electric current supply unit are the same.

2. The particle beam irradiation apparatus according to claim 1, wherein the scanning control unit has a transmission section configured to transmit an operation clock signal to the electric current supply unit, and
the electric current supply unit has a receiving section configured to receive the operation clock signal transmitted from the transmission section.

3. The particle beam irradiation apparatus according to claim 1, further comprising:
a position measuring unit configured to measure a position of the particle beam scanned by the scanning unit,
wherein the scanning control unit determines whether or not there is an abnormality in a scanning by the scanning unit, on the basis of a comparison result between a plan position of the particle beam corresponding to the electric current command value and a measurement position of the particle beam measured by the position measuring unit.

* * * * *